US011236366B2

(12) United States Patent
Broeker

(10) Patent No.: US 11,236,366 B2
(45) Date of Patent: Feb. 1, 2022

(54) PRODUCTION OF SQUALENE FROM HYPER-PRODUCING YEASTS

(75) Inventor: Michael Broeker, Marburg (DE)

(73) Assignee: NOVARTIS AG, Basel (CH)

( * ) Notice: Subject to any disclaimer, the term of this patent is extended or adjusted under 35 U.S.C. 154(b) by 808 days.

(21) Appl. No.: 13/061,505

(22) PCT Filed: Aug. 28, 2009

(86) PCT No.: PCT/IB2009/006825
§ 371 (c)(1),
(2), (4) Date: Jun. 10, 2011

(87) PCT Pub. No.: WO2010/023551
PCT Pub. Date: Mar. 4, 2010

(65) Prior Publication Data
US 2011/0243969 A1 Oct. 6, 2011

Related U.S. Application Data

(60) Provisional application No. 61/190,486, filed on Aug. 28, 2008.

(51) Int. Cl.
*C12P 5/02* (2006.01)
*C12P 5/00* (2006.01)

(52) U.S. Cl.
CPC .............. *C12P 5/02* (2013.01); *C12P 5/007* (2013.01)

(58) Field of Classification Search
None
See application file for complete search history.

(56) References Cited

U.S. PATENT DOCUMENTS

| 5,460,949 | A | * | 10/1995 | Saunders et al. | 435/55 |
| 8,092,813 | B1 | * | 1/2012 | Novicki | A61K 47/06 424/278.1 |
| 8,273,361 | B2 | * | 9/2012 | Reed | A61K 39/0011 424/282.1 |
| 8,367,395 | B2 | * | 2/2013 | Bailey | C11B 1/10 435/183 |
| 2004/0047882 | A1 | | 3/2004 | Broeker | |
| 2004/0235088 | A1 | | 11/2004 | Weber et al. | |
| 2012/0156249 | A1 | | 6/2012 | Lang et al. | |

FOREIGN PATENT DOCUMENTS

| JP | H05192184 A | 3/1993 |
| JP | H061-16171 A | 4/1994 |
| JP | H0690743 A | 5/1994 |
| JP | H10120548 A | 5/1998 |
| JP | 3283551 B2 | 5/2002 |
| JP | 2007-060975 A | 3/2007 |
| JP | 2008517610 A | 5/2008 |
| JP | 4126067 B2 | 7/2008 |
| WO | WO-1995/17209 A1 | 6/1995 |
| WO | WO-2006/045438 A1 | 5/2006 |
| WO | WO-2006/072175 A1 | 7/2006 |
| WO | WO-2007015167 A2 | 8/2007 |
| WO | WO-2008/056263 A2 | 5/2008 |
| WO | WO-2008/130372 A2 | 10/2008 |
| WO | WO-2009/143490 A | 11/2009 |

OTHER PUBLICATIONS

Bhattacharjee et al (World Journal of Microbiology and Biotechnology 19:605-608, 2003).*
Kamimura et al (Applied Microbiol Biotechnol, 42:35-357, 1994).*
Kurtzman et al, 2005 Technical Abstract).*
Basson et al Applied Microbiol Biotechnol, 53:30-35, 1999.*
Germann et al, (J. Biological Chemistry, 280:35904-13, 2005).*
Pasrija et al. (J. Antimicrob Chemother, 55(6):905-913, 2005).*
Bhattacharjee et al (World Journal of Microbiology and Biotechnology 17:811-816, 2001.*
BD Bionutrients™ Technical Manual: Advanced Bioprocessing, Third Edition Revised, Oct. 2006, 72 pages.
Bhattacharjee et al. (2003). "Extraction of squalene from yeast by supercritical carbon dioxide," *World J Microbiol Biotech* 19:605-608.
Bio Springer, (2007) "Animal free nutrients for fermentation and culture media," Available online: http://www.biospringer.com/cc_redirection_lien.php?cc-id=24.
Chang et al. (Feb. 26, 2008). "The isolation and characterization of *Pseudozyma* sp. JCC 207, a novel producer of squalene," *App Microbiol Biotech* 78:963-972.
Chemler et al. (2006). "Biosynthesis of isoprenoids, polyunsaturated fatty acids and flavonoids in *Saccharomyces cerevisiae*," *Microbial Cell Factories* 5:1-9.
Departement of Health & Human Services of the Food and Drug Administration USA (2000), Letter to Manufacturers of Biological Products, 2 pages.
Donald et al. (1997) "Effects of overproduction of the catalytic domain of 3-hydroxy-3-methylglutaryl coenzyme a reductase on squalene synthesis in *Saccharomyces cerevisiae*," Appl Env Microbiol 63:3341-3344.
Dow Agrosciences. (2006). "Using yeast fermentation to produce cost-effective and biodegradable lubricants," Dow Agrosciences LLC Status Report, pp. 1-4. Online at: http://statusreports.atp.nist.gov/reports/95-01-0148PDF.pdf.
EMEA The European Agency for the Evaluation of Medicinal Products, Committee for Veterinary Medicinal Products (1999), "Note for Guidance for Minimising the Risk of Transmitting Animal Spongiform Encephalopathy Agents via Veterinary Medicinal Products," 11 pages.
EMEA, "Questions and answers on bovine spongiform encephalopathies (BSE) and vaccines," (2001), 7 pages.
European Opposition filed Mar. 21, 2012 by Sanofi-Aventis Deutschland GmbH for EP 2268823, 31 pages.
European Search Report and Opinion mailed Jul. 22, 2011, for EP Application No. 11170769 filed Jun. 21, 2011, 12 pages.

(Continued)

Primary Examiner — Patricia Duffy
(74) Attorney, Agent, or Firm — Morrison & Foerster LLP

(57) ABSTRACT

A method for preparing purified yeast is disclosed, where the squalene source is a yeast that hyper-produces squalene. The squalene is useful for pharmaceutical purposes. For instance, it can be used to prepare an oil-in-water emulsion, and the emulsion is particularly suitable for use as an immunological adjuvant.

19 Claims, No Drawings

(56) References Cited

OTHER PUBLICATIONS

Germann, M. et al. (2005) "Characterizing sterol defect suppressors uncovers a novel transcriptional signaling pathway regulating zymosterol biosynthesis," The Journal of Biological Chemistry 280:35904-35913.
International Search Report mailed Mar. 17, 2010, for PCT/IB09/06825 filed Aug. 28, 2009, 4 pages.
Jahnke, L. and Klein, H.P. (1983) "Oxygen requirements for formation and activity of the squalene epoxidase in Saccharomyces cerevisiae," Journal of Bacteriology 155:488-492.
Kamimura et al. (1994) "Construction of squalene-accumulating Saccharomyces cerevisiae mutants by gene disruption through homologous recombination," Appl Microbiol Biotechnol 42:353-357.
Kuchta et al. (1997) "Inhibition of ergosterol biosynthesis is not accompanied by a change in fatty acid composition in Saccharomyces cerevisiae treated with the antifungal agent 6-amino-2-n-pentylthiobenzothiazole," FEMS Microbiol Letters 150:43-47.
Mantzouridou et al. (Jun. 19, 2009). "Squalene versus ergosterol formation using Saccharomyces cerevisiae: Combined effect of oxygen supply, inoculum size, and fermentation time on yield and selectivity of the bioprocess," J Agricult Food Chem 57:6189-6198.
Nishikawa et al. (1978) "Thiamine-induced alteration in sterol compositions of Saccharomyces carlsbergensis 4228," Biochimica et Biophysica Acta 531:86-95.
O'Hagan (2007). "MF59 is a safe and potent vaccine adjuvant that enhances protection against influenza virus infection," Expert Rev. Vaccines 6:699-710.
Pasrija et al. (2005) "Squalene epoxidase encoded by ERG1 affects morphogenesis and drug susceptibilities of Candida albicans," Journal of Antimicrobial Chemotherapy 55:905-913.
Polakwski et al. (1999) "Enhanced sterol-acyl transferase activity promotes sterol accumulation in Saccharomyces cerevisiae," Appl. Microbiol. Biotechnol. 53:30-35.
Ryder et al. (1986) "Ergosterol biosynthesis inhibition by the thiocarbamate antifungal agents tolnaftate and tolciclate," Antimicrobial Agents and Chemotherapy 29:858-860.
Ryder, N.S. and Dupont, M.-C. (1985) "Inhibition of squalene epoxidase by allylamine antimycotic compounds," Biochem. J. 230:765-770.
Sanati et al. (1997) "A new triazole, voriconazole (UK-109,496), blocks sterol biosynthesis in Candida albicans and Candida krusei," Antimicrobial Agents and Chemotherapy 41 :2492-2496.
Sax K.J. and Stross F.H. (1957). "Squalene: A Standard," Analytical Chemistry 29:1700-1702.
Spanova et al. (Jul. 8, 2008). "Squalene storage and subcellular distribution in the yeast Saccharomyces cerevisiae," Chem Phys Lip 154S:S35.
Zhang J. and Greasham R., (1999). "Chemically defined media for commercial fermentations," Appl. Microbiol. Biotechnol. 51:407-421.
Lang and Looman (1995). "Efficient expression and secretion of Aspergillus niger RH5344 polygalacturonase in Saccharomyces cerevisiae," Appl. Microbiol. Biotechnol. 44:147-156.
ATCC Product Sheet, Cell Culture Media "ATCC Medium: 790 by+ Medium" 1 page. Cited in the European Reply to Opposition filed Nov. 5, 2012 by Novartis AG for EP2268823.
BD Bionutrients Technical Manual (Oct. 2006), "Bacto Peptone," p. 34.
Bondioli et al. (1993). "Squalene Recovery from Olive Oil Deodorizer Distillates," J. Amer. Oil Chemists, 70(8): 763-776.
Certificate of Analysis of Fluka squalene, by Sigma-Aldrich, Sep. 1, 2004. 1 page.
Certificate of Analysis of Fluka squalene, by Sigma-Aldrich, Oct. 15, 2004. 1 page.
EMEA, The European Agency for the Evaluation of Medicinal Products, Committee for Proprietary Medicinal Products and Committee for Veterinary Medicinal Products (2004). "Note for Guidance for Minimising the Risk of Transmitting Animal Spongiform Encephalopathy Agents via Veterinary Medicinal Products," 14 pages.
EMEA, The European Agency for the Evaluation of Medicinal Products, Cervarix (2007). "Scientific Discussion," 56 pages.
EMEA, The European Agency for the Evaluation of Medicinal Products, Gardasil (2006). "Scientific Discussion," 40 pages.
Decision to Discontinue Opposition Proceedings for EP2268823, Feb. 11, 2013, 2 pages.
Reply to Opposition filed Nov. 5, 2012 by Novartis AG for EP2268823, 11 pages.
He et al. (2002). "Extraction and Purification of Squalene from Amaranthus Grain," J. Agric. Food Chem 50(2): 368-372.
Leber et al. (2001). "A novel sequence element is involved in the transcriptional regulation of expression of the ERG1 (squalene epoxidase) gene in Saccharomyces cerevisiae," Eur. J. Biochem. 268: 914-924.
Owen (2009). "Sharks Killed for Oil Used in Swine Flu Vaccine," National Geographic Daily News. 5 pages.
Sigma-Aldrich (2012). "Protein Sources A to Z." 3 pages.
Withdrawal of Opposition filed Nov. 28, 2012 by Sanofi-Aventis Deutschland GmbH for EP2268823, 1 page.
World Health Organization (2006). "Squalene-based adjuvants in vaccines," 2 pages.
Japanese Office Action, dated Jan. 29, 2016, for JP Application No. 2012-36971, 10 pages.
Ott et al. (1995). "Enhancement of humoral response against human influenza vaccine with the simple submicron oil/water emulsion adjuvant MF59." Vaccine 13.16:1557-1562.
Fox et al. (2008). "Monitoring the effects of component structure and source on formulation stability and adjuvant activity of oil-in-water emulsions." Colloids and Surfaces B: Biointerfaces 65:98-105.
Pietsch et al. (2007). "Concentration of squalene from shark liver oil by short-path distillation." Eur. J. Lipid Sci. Technol. 109: 1077-1082.
Valachovic et al. (2007). "Biosynthetic Approaches to Squalene Production: The Case of Yeast." Methods in Molecular Biology book series, 1494:95-106.

\* cited by examiner

PRODUCTION OF SQUALENE FROM HYPER-PRODUCING YEASTS

CROSS REFERENCE TO RELATED APPLICATIONS

This application is a U.S. National Phase patent application of PCT/IB2009/006825, filed Aug. 28, 2009, which claims priority to U.S. Provisional patent application Ser. No. 61/190,486, filed Aug. 28, 2008, all of which are hereby incorporated by reference in the present disclosure in their entirety.

This application claims the benefit of U.S. provisional application 61/190,486, the complete contents of which are hereby incorporated herein by reference.

TECHNICAL FIELD

This invention is in the field of manufacturing squalene e.g. for use in oil-in-water emulsions.

BACKGROUND ART

Shark liver oil contains a branched, unsaturated terpenoid called squalene, 2,6,10,15,19,23-hexamethyl-2,6,10,14,18,22-tetracosahexaene. Squalene is known for use in oil-in-water emulsions in human vaccines, for instance the MF59 emulsion that is used for adjuvanting influenza vaccines. Squalene is also used in other pharmaceutical products (e.g. ointments, suppositories) and in cosmetics.

Current sources for squalene are primarily fish oils, and in particular shark liver oils. There can be problems associated with the use of squalene extracted from shark liver oil, particularly if rigorous manufacturing standards (such as those used during the production of MF59 by Novartis) are not upheld. For instance, sharks may be infected by pathogens that are also infectious for humans or that produce substances that are harmful to humans, and TSE or TSE-like shark agents may exist [e.g. references 1-3]. Furthermore, sharks can contain human toxins, such as carchatoxin. Thus cheap low-grade sources of squalene are not suitable for human pharmaceutical use. The risk of harm to a human recipient may be heightened in situations where the squalene is part of an immunological adjuvant because, by definition, the adjuvant may induce a strong unwanted immune response against the impurity.

Rather than use cheap low-grade sources of shark-derived squalene, therefore, pharmaceutical uses of squalene (e.g. as used in the manufacture of MF59) utilise a higher grade material, but these high quality squalenes are expensive and of limited availability. Such expensive sources are not useful, for instance, for use in the developing world.

It would be useful to find a source of squalene which meets these high pharmaceutical standards without being so expensive. A viable alternative source of squalene is therefore desirable, particularly when the squalene is intended for parenteral use in humans and/or for use in an immunological adjuvant. A cheaper source of pharmaceutical-grade squalene would be of particular use in developing countries which either have no ready access to sharks or cannot easily afford the expensive pharmaceutical-grade material currently used e.g. by Novartis.

DISCLOSURE OF THE INVENTION

The invention relates to methods for preparing squalene from yeasts that hyper-produce squalene. Yeasts are GRAS organisms (generally regarded as safe) and so are a useful source of squalene for pharmaceutical use. Moreover, the squalene can be prepared free from contamination by pathogens, prions and environmental toxins e.g. yeasts are a priori mercury-free. In the vaccine field yeasts are already used (e.g. for recombinant expression of hepatitis B virus surface antigen) and so do not present any particular regulatory concerns i.e. yeast-derived squalene is particularly suitable for use in preparing immunological adjuvants. Finally, yeast culture techniques are widespread and readily amenable to technology transfer.

Thus the invention provides a process for preparing pure squalene, comprising the steps of: (a) growing a yeast that produces a high yield of squalene during culture; and (b) purifying squalene from the yeast grown in step (a). The purified squalene can be used as a component in preparation of pharmaceuticals, foods, food additives, cosmetics, etc.

The invention also provides a process for preparing a squalene-containing product, comprising the steps of: (a) obtaining squalene that has been purified from a yeast that produces a high yield of squalene during culture; and (b) combining the squalene of step (a) with a non-squalene component to form the squalene-containing product.

The invention also provides the use of a yeast that produces a high yield of squalene during culture, for the production of purified squalene.

The invention also provides a process for preparing purified squalene, comprising the steps of: (a) growing a yeast culture under conditions such that the yeast produces a high yield of squalene; (b) purifying squalene from the cultured yeast, such that the squalene is ≥97% pure by weight The invention also provides a process for preparing an oil-in-water emulsion, comprising the steps of: (a) purifying squalene from a yeast that produces a high yield of squalene during culture; and (b) combining the squalene purified in step (a) with an aqueous component to form the oil-in-water emulsion.

Thus the invention provides a process for preparing an oil-in-water emulsion, comprising the steps of: (a) obtaining squalene that has been purified from a yeast that produces a high yield of squalene during culture; and (b) combining the squalene of step (a) with an aqueous component to form the oil-in-water emulsion.

The invention also provides a process for preparing an immunogenic composition (e.g a vaccine), comprising preparing an oil-in-water emulsion as described above, and mixing the emulsion with an immunogen.

The invention also provides a process for preparing a kit for preparing an immunogenic composition in this manner, comprising preparing an oil-in-water emulsion as described above, packaging the emulsion in a first container, and combining the first container in kit form with a second container, wherein the second container contains an immunogen. The immunogen may be in dried or aqueous form.

The invention also provides a process for raising an immune response in an animal (e.g. in a mammal), comprising administering an immunogenic composition prepared in such ways to the animal.

The invention also provides squalene for use in the manufacture of a medicament for raising an immune response in a mammal, wherein the squalene is (i) purified from a yeast that produces a high yield of squalene during culture and (ii) combined with an aqueous component to form an oil-in-water emulsion for inclusion in the medicament.

The invention provides a process for preparing an oil-in-water emulsion, comprising the steps of: (a) growing a yeast culture under conditions such that the yeast produces a high yield of squalene; (b) purifying squalene from the cultured yeast; and (c) combining the squalene purified in step (b) with an aqueous component to form the oil-in-water emulsion.

The invention also provides, in a process that uses squalene, the improvement consisting of using squalene purified from a yeast that produces a high yield of squalene during culture.

Squalene Production in Yeast

The invention uses squalene that is purified from yeast. The yeasts may be naturally-occurring or mutant strains that are selected for a high squalene yield, but they will generally be genetically engineered strains that have been manipulated to produce squalene in high yields. Another possibility is to culture natural, mutant or engineered yeast strains in the presence of factors that result in increased squalene yield.

The yield of squalene can be expressed as a % of cell dry weight (cdw) in a particular yeast. A normal yeast wild-type *Yarrowia lipolytica* strain can typically produce squalene at about 0.5% cdw, whereas a normal *Saccharomyces uvarum* brewer's yeast can produce squalene at about 1.4% cdw [4]. A yeast that produces a "high yield" of squalene is one in which at least 2% cdw is squalene e.g. ≥3%, ≥4%, ≥5%, ≥6%, ≥7%, ≥8%, ≥9%, ≥10%, ≥11%, ≥12%, ≥13%, ≥14%, ≥15% or more of cdw.

Squalene yield can also be expressed as a % of total lipid in a particular yeast. A normal *S.uvarum* brewer's yeast produces squalene at 33% of total lipids [4]. A yeast that produces a "high yield" of squalene may produce squalene at ≥40% of total lipids e.g. ≥50%, ≥60%, etc.

The squalene is advantageously at least 95% in its trans-configuration (natural isoform) e.g. ≥96%, ≥97%, ≥98%, ≥99%, or 100%.

Naturally-occurring mutant yeast strains that have a high yield of squalene are known in the art, for example the *Torulasopra delbrueckii* strain described in reference 5. Mutants can be obtained by well known methods of inducing mutations (either random or directed mutagenesis), for example those described in references 6 and 7, followed by screening of the mutagenised cells for those with a suitably high squalene yield. Reference 8 describes mutant yeast strains with temperature-sensitive mutations of 4-α-carboxysterol-C3-dehydrogenase (ERG26) that result in squalene accumulation when grown at an appropriate temperature.

Usually, though, the invention will use genetically engineered yeasts. Various methods can be used to increase the squalene yield of a starting strain. Sterol metabolism can be manipulated to increase squalene yields e.g. by increasing squalene anabolism, and/or by decreasing squalene catabolism (including its breakdown and/or its natural conversion to ergosterol). Genes involved in squalene biosynthesis include mevalonate kinase, phosphomevalonate kinase, pyrophosphomevalonate decarboxylase, isopentenyl pyrophosphate isomerase, HMGR (3-hydroxy-3-methylglutaryl-CoA reductase), and squalene synthase. Genes involved in the conversion of squalene to ergosterol include squalene epoxidase (ERG1), lanosterol synthase, C14-dimethylase, d14-reductase, C4-methyloxidase, C4-decarboxylase (ERG26), 3-ketoreductase, C24-methyltransferase, C8-isomerase, C5-desaturase, d22-desaturase and d24-reductase. Other catabolic enzymes include LEU2 (β-isopropylmalate dehydrogenase), oxidosqualene cyclase, zymosterol-24-methyltransferase and ergosta-5,7,24(28)-trienol-22-dehydrogenase. Such manipulations are disclosed e.g. in reference 9.

Activity levels for the relevant enzymes can be increased or decreased in any suitable manner, usually by genetic engineering. Yeast can be genetically engineered by standard methods, including those described in reference 7 & 10. Genes can be introduced into yeasts in various ways e.g. in a plasmid, or by chromosomal integration. Gene knockout techniques are also well established for yeasts.

Ways of increasing enzymatic activity include, but are not limited to: increasing the copy number of an enzyme that is already present in a strain e.g. by adding one or more further genes, usually on a plasmid; increasing the expression levels (hyper-expression) of an enzyme that is already present e.g. by providing it with a stronger promoter; adding a heterologous enzyme i.e. one that is not already present in a strain; decreasing or preventing expression of an inhibitory or suppressor factor; by modifying the sequence of an enzyme that is already present in a strain e.g. to enhance stability, to remove amino acid residues that effect inhibition, to change protein trafficking or cellular location; etc. For example, it is known that truncation of an enzyme's sequence can change it from a membrane protein to a cytosolic protein such that it causes squalene accumulation.

Ways of decreasing enzymatic activity include, but are not limited to: deletion of an enzyme that is already present in a strain; decreasing the expression levels of an enzyme that is already present e.g. by providing it with a weaker promoter; increasing expression of an inhibitory or suppressor factor; by modifying the sequence of an enzyme that is already present in a strain e.g. to decrease stability, to modify amino acid residues that mediate enzymatic activity, to delete functional domains, to change protein trafficking or cellular location; etc.

Levels of under- or over-expression, and of increased or decreased activity, are expressed relative to the corresponding wild-type strain lacking the relevant modification.

There are already several reports of suitable genetic manipulations in yeast. For example, reference 11 discloses yeasts with increased squalene accumulation due to hyper-expression of HMGR with decreased expression of zymosterol-24-methyltransferase and/or ergosta-5,7,24(28)-trienol-22-dehydrogenase. Reference 12 discloses yeasts which express a truncated HMGR (the HMG1 isoenzyme) that lacks its membrane-binding region, thus providing a cytosolic enzyme, and exhibit squalene accumulation. Disruption of squalene epoxidase causes accumulation of squalene [13]. Reference 14 discloses modification of *Yarrowia lipolytica* to inhibit acetyl-CoA carboxylase and to hyper-express HMGR, such that the strains produced squalene at 2% cdw using inexpensive carbon sources such as cheese whey or sugar cane. Mutation of oxidosqualene cyclase (ERG7) can also cause squalene accumulation [8]. An ergosterol auxotroph unable to grow on 3-ketosterols without the addition of cholesterol has been found to accumulate squalene [15]. Yeast strains with impaired heme synthesis can accumulate squalene [16].

A combination of these approaches may be used e.g. expression of cytosolic truncated HMGR in combination with knockout of squalene epoxidase.

*S.cerevisiae* strains that express truncated HMGR are preferred, such as those described in reference 12. Expression of a soluble non-membrane-bound form of HMG1, ideally under the control of a constitutive promoter (e.g. an ADH1 promoter), leads to a high level of squalene accumulation (40× wild-type). The truncated protein may contain part of the spacer region and the C-terminal catalyitic domain of HMG1p but lack the N-terminal membrane-spanning region. A strain may express one or more copies of the gene.

Yeast (natural, mutant or engineered) can be grown in the presence of factors that increase the yield of squalene. For instance, allylamine antimycotics (e.g. terbinafine, naftifine) can inhibit squalene epoxidase resulting in ergosterol deficiency and an accumulation of intracellular squalene [17]. If squalene epoxidase inhibitors are included at a sub-lethal level, or are used with resistant strains, etc., the squalene yield of a culture can be increased. An increase of squalene yield of ~100-fold was seen in reference 18 in the presence of terbinafine. Squalene epoxidases in difference *Candida* species differ in sensitivity to terbinafine by a factor of about 10 and so the concentration of a factor may have to be optimised for any yeast of interest. Other antimycotics that can cause squalene accumulation include, but are not limited to, voriconazole [19],6-amino-2-n-pentylthiobenzothiazole [20], and thiocarbamate antimycotics (e.g. tolnaftate and tolciclate) [21]. Growth in the presence of thiamine can also increase squalene yield [22].

Suitable yeasts include any yeast that produces squalene or that can be manipulated to produce squalene. Examples of suitable yeasts include species from the genera *Arthroascus, Arxiozyma, Arxula, Bullera, Candida, Debaryomyces, Dekkera, Dipodascopsis, Endomyces, Eremothecium, Geotrichum, Hanseniaspora, Hansenula, Hornioascus, Issatchenkia, Kloeckera, Kluyveromyces, Lipomyces, Lodderomyces, Metschnikowia, Pachysolen, Pachytichospora, Pichia, Rhodosporidium, Rhodotorula, Saccharomyces, Saccharomycodes, Schizoblastosporion, Schizosaccharomyces, Schwaniomyces, Sporobolomyces, Sterigmatomyces, Sympodiomyces, Taphrina, Torula, Torulaspora, Torulopsis, Trichosporon, Yarrowia, Zygohansenula,* and *Zygosaccharomyces*. Useful genera for the invention are *Saccharomyces,* and *Torulaspora*. A preferred species for use with the invention are *Torulaspora delbrueckii* and most preferred is *Saccharomyces cerevisiae*.

Yeast fermentation to produce squalene can be carried out on a large scale, giving almost unlimited amounts of squalene and thus reducing the unit cost of the squalene produced. The yeast can be grown using any known culture or fermentation system. Suitable yeast fermentation systems for use in the invention include batch and continuous fermentation systems. A two-stage culture system may be used. The yeast can be grown under aerobic conditions to increase biomass before being changed to an (at least partially) anaerobic phase to increase squalene production. A two-stage culture system allows squalene accumulation to be separated from the growth phase. Culture of yeast under anaerobic conditions can be used to increase squalene production [23-25], and carbon sources may also have an influence.

Because yeast can be grown on a controlled medium a culture can assuredly be free from disease-causing agents, environmental toxins and other contaminants. Suitable media for growing yeast will depend on the yeast species and fermentation system. Suitable media include rich or minimal media, with and without supplements. For example, the yeast may be grown in MM, EMM, YPD, YPDS, YPG, YPGS, YT, YAPD, YEPD, YPL, YEP, YNBD and SD. Media free from any animal-origin products (e.g. whey) are ideal. If animal (and particularly bovine) materials are used during culture of cells, they should be obtained from sources that are free from transmissible spongiform encaphalopathies (TSEs), and in particular free from bovine spongiform encephalopathy (BSE).

Due to the control of culture conditions, squalene purified from yeast according to the invention is free from contamination by pathogens, metabolic products of pathogens, toxins and other detrimental substances, and is a priori free from TSE-causing agents (such agents are not found in yeasts). Methods for isolating squalene from yeast are known in the art and include methods such as chromatography, liquid-liquid solvent extraction, subcritical gas extraction [26], and supercritical fluid extraction (optionally preceded by lyophilisation) e.g. using $CO_2$, chloroform-methanol solvent extraction [5,23,27]. Ideally, the purified squalene is greater than 97% pure (by weight), more preferably, greater than 98%, 99%, 99.5%, 99.9%, 99.99%, even 100% pure. Ideally, the purified squalene contains less than 6153 pg of PCB/dioxin per gram of squalene, measured as toxic equivalents (TEQ). TEQs allow the toxicity of a mixture of PCBs/dioxins to be represented as a single number. The toxicity of each PCB (polychlorinated biphenyl) is expressed as a fraction (the toxic equivalency factor, TEF; WHO 2005) of the toxicity of 2,3,7,8-TCDD dioxin (which has a reference value of 1). To calculate the total TEQ of a mixture, the mass of each PCB is multiplied by its TEF and then the TEQ is the sum of these values. For instance, the squalene may have dioxin/PCB levels less than 5000 pg/g, 4000 pg/g, 3000 pg/g, 2000 pg/g, 1000 pg/g, 500 pg/g, 100 pg/g, 50 pg/g (TEQ).

Once the squalene has been purified from the yeast it can be used for preparation of downstream products e.g. medicines, oil-in-water emulsion adjuvants, etc.

Oil-in-Water Emulsions

Oil-in-water emulsions have been found to be particularly suitable for use in adjuvanting vaccines. Emulsions prepared according to the invention include squalene and at least one surfactant, in addition to an aqueous component. The emulsions may contain additional oils. Ideally, the oil(s) and surfactant(s) are biodegradable (metabolisable) and biocompatible.

Oil combinations of squalene and tocopherols can be used. Where a composition includes a tocopherol, any of the $\alpha, \beta, \gamma, \delta, \epsilon,$ or $\xi$ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. A preferred α-tocopherol is DL-α-tocopherol.

An oil content in the range of 2-20% (by volume) is typical.

The oil droplets in the emulsion are generally less than 5 µm in diameter, and may even have a sub-micron diameter, with these small sizes conveniently being achieved with a microfluidiser to provide stable emulsions. Droplets with a size less than 220 nm are preferred as they can be subjected to filter sterilization.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear BO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Nonionic surfactants are preferred. The most preferred surfactant for including in the emulsion is polysorbate 80 (polyoxyethylene sorbitan monooleate; Tween 80).

Mixtures of surfactants can be used e.g. Tween 80/Span 85 mixtures. A combination of a polyoxyethylene sorbitan ester and an octoxynol is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 2%; octyl- or nonylphenoxy polyoxyethanols (such as Triton X-100, or other Triton series detergents) 0.001 to 0.1%; polyoxyethylene ethers (such as laureth 9) 0.1 to 20%.

Squalene-containing oil-in-water emulsions containing polysorbate 80 surfactant are preferred. Specific oil-in-water emulsion adjuvants that can be made using squalene purified according to the invention include, but are not limited to:

A submicron emulsion of squalene, polysorbate 80, and sorbitan trioleate. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [28-30], as described in more detail in Chapter 10 of ref. 31 and chapter 12 of ref. 32. The MF59 emulsion advantageously includes citrate ions e.g. 10 mM sodium citrate buffer.

A submicron emulsion of squalene, a tocopherol, and polysorbate 80. These emulsions may have from 2 to 10% squalene, from 2 to 10% tocopherol and from 0.3 to 3% polysorbate 80, and the weight ratio of squalene:tocopherol is preferably≤1 (e.g. 0.90) as this can provide a more stable emulsion. Squalene and polysorbate 80 may be present at a volume ratio of about 5:2 or at a weight ratio of about 11:5. One such emulsion can be made by dissolving Tween 80 in PBS to give a 2% solution, then mixing 90 ml of this solution with a mixture of (5 g of DL-a-tocopherol and 5 ml squalene), then microfluidising the mixture. The resulting emulsion has submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [33].

An emulsion of squalene, a tocopherol, and a Triton detergent (e.g. Triton X-100). The emulsion may also include a 3d-MPL (see below). The emulsion may contain a phosphate buffer.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [34]. The emulsion may also include one or more of: alditol; a cryoprotective agent (e.g. a sugar, such as dodecylmaltoside and/or sucrose); and/or an alkylpolyglycoside. The emulsion may include a TLR4 agonist [35]. Such emulsions may be lyophilized.

An emulsion of squalene, poloxamer 105 and Abil-Care [36]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

The emulsions can be mixed with a separate antigen-containing component extemporaneously, at the time of delivery, or during vaccine manufacture. Where these two components are liquids then the volume ratio of the two liquids for mixing can vary (e.g. between 5:1 and 1:5) but is generally about 1:1.

Thus a process of the invention may include a further step of combining the emulsion with an immunogen. The process may include a further step of packaging the emulsion or the emulsion/immunogen mix. An emulsion produced according to the invention may be packaged in a first container within a kit, where the kit includes a second container including an immunogen. The contents of the two containers may be mixed and then administered to a subject (e.g. human) or may be separately co-administered.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

MODES FOR CARRYING OUT THE INVENTION

Various mutant yeast strains are prepared by genetic engineering techniques. The mutant strains either over-express or under-express enzymes involved in squalene metabolism. One such yeast is the ATC1551 strain disclosed in reference 11, which can produce squalene at up to 16% cdw under appropriate growth conditions.

After culture, the cultured cells are collected and disrupted using a glass bead mill. Squalene is purified from the lysate either by (2:1) chloroform-methanol solvent extraction or, to improve yield, by the method disclosed in reference 5 using lyophilisation and then supercritical carbon dioxide extraction. Resulting squalene is highly pure (>95%).

The purified squalene is combined with a mixture of Tween 80 and Span 85 surfactants and with a citrate buffer to prepare a mixture having 5% squalene, 0.5% Tween 80 and 0.5% Span 85 (by volume). This mixture is microfluidised to prepare an emulsion having an average droplet size of less than 500 nm. This emulsion, known as 'MF59', can be used as a vaccine adjuvant.

It will be understood that the invention has been described by way of example only and modifications may be made whilst remaining within the scope and spirit of the invention.

REFERENCES

[1] Borucinska & Frasca (2002) *J Fish Diseases* 25:287-98.
[2] Bertone et al. (1996) *J Fish Diseases* 19:429-34.
[3] Briones et al. (1998) *J Vet Med B* 45:443-5.

[4] Blagovic et al. (2001) *Food technol. Biotechnol.* 39:175-81.
[5] Bhattacharjee et al (2003) *World Journal of Micorbiology and Biotechnology,* 19: 605-608.
[6] Boeke et al., (1984) Mol. Gen. Genet., 197:345-346
[7] Sherman et al., (1986) Methods and Yeast Genetics, Cold Spring Harbor Laboratory, N.Y.
[8] Germann et al. (2005) *J Biol Chem* 280:35904-13.
[9] Veen et al. (2003) *FEMS Yeast Research* 4:87-95.
[10] Sambrook, J., Fritsch, E. F. & Maniatis, T (1989). *Molecular cloning: a laboratory manual.* Cold Spring Harbor Press. Cold Spring Harbor
[11] U.S. Pat. No. 5,460,949.
[12] Polakowski et al. (1998) *Appl Microbiol Biotechnol* 49(1):66-71.
[13] Pasrija et al. (2005) *J Antimicrob Cheinother.* 55(6): 905-13.
[14] *Performance of the Third* 50 *Completed ATP Projects* (2006) NIST SP 950-4, pages 59-62.
[15] Gachotte et al. (1999) *PNAS USA* 96:12655-60.
[16] Ness et al. (1998) *J Bacteriol.* 180(7):1913-9.
[17] Ryder et al. (1985) *Biochem J.* 230:765-770
[18] Leber et al. (2001) *European Journal of Biochemistry* 268:914-924.
[19] Sanati et al. (1997) *Antimicrob Agents Chemother.* 41(11):2492-6.
[20] Kuchta et al. (1997) *FEMS Microbiol Lett* 150:43-7.
[21] Ryder et al. (1986) *Antimicrob Agents Chemother* 20:858-60.
[22] Nishikawa et al. (1978) *Biochim Biophys Acta* 531(1): 86-95.
[23] Bhattacharjee et al, (2001) World Journal of Micorbiology and Biotechnology, 17: 811-816
[24] Jahnke & Klein (1983) *J Bacteroil* 155:488-92.
[25] Valero et al. (2001) *J Bioscience Bioengin* 92:33-8.
[26] WO94/26683.
[27] Foch et al., (1957) Journal of Biological Chemistry, 226:497-509.
[28] WO90/14837.
[29] Podda & Del Giudice (2003) *Expert Rev Vaccines* 2:197-203.
[30] Podda (2001) *Vaccine* 19:2673-2680.
[31] *Vaccine Design: The Subunit and Adjuvant Approach* (eds. Powell & Newman) Plenum Press 1995 (ISBN 0-306-44867-X).
[32] *Vaccine Adjuvants: Preparation Methods and Research Protocols* (Volume 42 of *Methods in Molecular Medicine* series). ISBN: 1-59259-083-7. Ed. O'Hagan.
[33] WO2008/043774.
[34] US-2007/0014805.
[35] US-2007/0191314.
[36] Suli et al. (2004) *Vaccine* 22(25-26):3464-9.

The invention claimed is:

1. A process for preparing an oil-in-water emulsion for parenteral use in humans, comprising the steps of: (a) providing a yeast culture that comprises a controlled medium free from animal-origin products cultured under conditions so that the yeast comprises at least 2% cell dry weight squalene; (b) purifying the squalene from the culture for parenteral use in humans such that it is of a pharmaceutical grade; and (c) combining the squalene purified in step (b) with an aqueous component to form the oil-in-water emulsion for parenteral use in humans, wherein the yeast is a modified strain (1) that expresses a truncated 3 hydroxy-3-methylglutaryl-CoA reductase (HMGR) enzyme that has a cytosolic location, and/or (2) that, relative to an unmodified parent strain, hyper-expresses HMGR.

2. A process for preparing an oil-in-water emulsion for parenteral use in humans, comprising the steps of: (a) obtaining squalene that has been purified for parenteral use in humans such that it is of a pharmaceutical grade from a yeast culture that comprises a controlled medium free from animal-origin products cultured under conditions so that the yeast comprises at least 2% by dry weight squalene; and (b) combining the squalene purified of step (a) with an aqueous component to form the oil-in-water emulsion for parenteral use in humans, wherein the yeast is a modified strain (1) that expresses a truncated 3 hydroxy-3- methylglutaryl-CoA reductase (HMGR) enzyme that has a cytosolic location, and/or (2) that, relative to an unmodified parent strain, hyper-expresses HMGR.

3. The process of claim 2, wherein the culture comprises squalene at >5% cell dry weight.

4. The process of claim 2, wherein the yeast is a *Saccharomyces*.

5. The process of claim 2, wherein the yeast expresses the truncated 3 hydroxy-3-methylglutaryl-CoA reductase (HMGR) enzyme that has a cytosolic location.

6. The process of claim 2, wherein the yeast hyper-expresses HMGR relative to the unmodified strain.

7. The process of claim 2, wherein the yeast is a modified strain that, relative to an unmodified parent strain, under-expresses zymosterol-24-methyltransferase and/or ergosta-5,7,24(28)-trienol-22-dehydrogenase.

8. The process of claim 2, wherein the conditions include the yeast expressing a mutant oxidosqualene cyclase.

9. The process of claim 2, wherein the conditions include the yeast having a disrupted squalene epoxidase.

10. The process of claim 2, wherein the conditions include the presence of a factor that increases squalene yield during culture.

11. The process of claim 10, wherein the factor is an allylamine, voriconazole, 6-amino-2-n-pentylthiobenzothiazole, thiamine, or a thiocarbamate.

12. The process of claim 2, wherein the conditions include partial or complete anaerobic conditions prior to squalene purification.

13. The process of claim 2, wherein the oil-in-water emulsion has oil droplets with a sub-micron diameter.

14. The process of claim 2, wherein the oil-in-water emulsion is a microfluidised emulsion.

15. The process of claim 2, wherein the oil-in-water emulsion comprises squalene and polysorbate 80.

16. A process for preparing a vaccine for parenteral use in humans, comprising a step of preparing an oil-in-water emulsion adjuvant by the process of claim 2 to prepare an oil-in-water emulsion suitable for use as an adjuvant, and mixing the oil-in-water emulsion adjuvant with an immunogen.

17. A process for preparing a kit for preparing an immunogenic composition, comprising preparing an oil-in-water emulsion for parenteral use in humans by the process of claim 2, packaging the emulsion in a first container, and combining the first container in kit form with a second container, wherein the second container contains an immunogen.

18. A process for raising an immune response in a mammal, comprising administering to the mammal a vaccine prepared (i) by the process of claim 16, or (ii) by using the kit of claim 17 by combining the emulsion in the first container of the kit with the immunogen in the second container of the kit.

19. The process of claim 4, wherein the yeast is a *Saccharomyces cerevisiae*.

\* \* \* \* \*